United States Patent [19]

Goldstein et al.

[11] Patent Number: 5,478,738
[45] Date of Patent: Dec. 26, 1995

[54] PURIFICATION OF αN-ACETYLGALACTOSAMINIDASE

[75] Inventors: Jack Goldstein, New York; Rosa S. Hurst, Staten Island, both of N.Y.

[73] Assignee: New York Blood Center, Inc., New York, N.Y.

[21] Appl. No.: 194,116

[22] Filed: Feb. 8, 1994

Related U.S. Application Data

[63] Continuation of Ser. No. 964,756, Oct. 22, 1992, abandoned.

[51] Int. Cl.$^6$ .................................................. C12N 9/26
[52] U.S. Cl. ...................... 435/201; 435/200; 435/814
[58] Field of Search ...................................... 435/200, 201, 435/814

[56] References Cited

U.S. PATENT DOCUMENTS

| | | |
|---|---|---|
| 4,330,619 | 5/1982 | Goldstein . |
| 4,427,777 | 1/1984 | Goldstein . |
| 4,609,627 | 9/1986 | Goldstein ................................ 435/200 |

OTHER PUBLICATIONS

"Single–Unit Transfusions of RBC Enzymatically Converted from Group B to Group O To A and O Normal Volunteers", by Lenny et al., in *Blood*, vol. 77, No. 6, pp. 1383–1388 (Mar. 15, 1991).

Itoh et al *J. Biochem* 95 pp. 959–970 1984 α–N–acetylgalactosaminidase from Squid Liver.

"Glycosidases of Ehrlich Ascites Tumor Cells and Ascitic Fluid–Purification and Substrate Specificity of α–N–Acetylgalactosaminidase and α–Galactosidase: Comparision with Coffee Bean α–Galactosidase", by Yagi et al., in *Archives of Biochemistry and Biophysics*, vol. 280, No. 1, pp. 61–67 (Jul. 1990).

"Affinity Purification of α–Galactosidase A From Human Spleen, Placenta and Plasmid With Elimination of Pyrogen Contamination", by Bishop et al., in *The Journal of Biological Chemistry*, vol. 286, No. 3, pp. 1307–1316 (Feb. 10, 1981).

*Primary Examiner*—Irene Marx
*Attorney, Agent, or Firm*—Amster, Rothstein & Ebenstein

[57] ABSTRACT

This invention relates to an improved method of purifying the enzyme α-N-acetylgalactosaminidase from avian liver, as well as to the purified enzyme. The enzyme is capable of removing A antigens from the surface of cells in blood products. The method of purifying the enzyme is simple and time efficient, and lends itself to large scale production.

25 Claims, No Drawings

PURIFICATION OF α N-ACETYLGALACTOSAMINIDASE

STATEMENT OF GOVERNMENT INTEREST

This invention was made with government support under NMRDC Grant No. N00014-90-J-1638. As such, the government has certain rights in this invention. This is a continuation of application Ser. No. 07/964,756 filed Oct. 22, 1992, now abandoned.

FIELD OF THE INVENTION

This invention relates to the purification of an enzyme for use in the conversion of type A and AB blood products to type O blood products. More particularly, this invention is directed to an improved method of purifying the enzyme a-N-acetylgalactosaminidase from avian liver, such purified enzyme being capable of removing the terminal moiety of the A-antigenic determinant from the surface of cells in blood products, while allowing the structure and function of the cells to remain intact. The blood products containing cells free of the A antigen are thereby rendered useful in transfusion therapy in the manner of 0 type blood.

BACKGROUND OF THE INVENTION

As used herein, the term "blood products" includes whole blood and cellular components derived from blood, including erythrocytes (red blood cells) and platelets.

There are more than thirty blood group systems, one of the most important of which is the ABO system. This system is based on the presence or absence of antigens A and/or B. Blood of group A contains antigen A on its erythrocytes. Similarly, blood of group B contains antigen B on its erythrocytes. Blood of group AB contains both antigens, and blood of group O contains neither antigen. These antigens are found on the surface of erythrocytes, which are red blood cells containing hemoglobin, the principal function of which is the transport of oxygen.

This invention is directed to the purification of an enzyme capable of removing the A antigens from the surface of cells in the blood products. There are three recognized major sub-types of blood type A. These sub-types are known as $A_1$, A intermediate ($A_{int}$) and $A_2$. There are both quantitative and qualitative differences which distinguish these three sub-types. Quantitatively, $A_1$ erythrocytes have more antigenic A sites, i.e., terminal N-acetyl-galactosamine residues, than $A_{int}$ erythrocytes which in turn have more antigenic A sites than $A_2$ erythrocytes. Qualitatively, the transferase enzymes responsible for the formation of A antigens differ biochemically from each other in $A_1$, $A_{int}$ and $A_2$ individuals. Some A antigens found in $A_1$ cells contain dual A antigenic sites. All three sub-type antigens must be removed in order to convert blood products from type A to type O thereby rendering the blood products universal for transfusion therapy.

Blood of group A contains antibodies to antigen B. Conversely, blood of group B contains antibodies to antigen A. Blood of group AB has neither antibody, and blood group O has both. A person whose blood contains either (or both) of the anti-A or anti-B antibodies cannot receive a transfusion of blood containing the corresponding incompatible antigen(s). If a person receives a transfusion of blood of an incompatible group, the blood transfusion recipient's antibodies coat the red blood cells of the transfused incompatible group and cause the transfused red blood cells to agglutinate, or stick together. Transfusion reactions and/or hemolysis (the destruction of red blood cells) may result therefrom.

In order to avoid red blood cell agglutination, transfusion reactions and hemolysis, transfusion blood type is cross-matched against the blood type of the transfusion recipient. For example, a blood type A recipient can be safely transfused with type A blood which contains compatible antigens. Because type O blood contains no A or B antigens, it can be transfused into any recipient with any blood type, i.e., recipients with blood types A, B, AB or O. Thus, type O blood is considered "universal", and may be used for all transfusions. Hence, it is desirable for blood banks to maintain large quantities of type O blood. However, there is a paucity of blood type O donors. Therefore, it is useful to convert types A, B and AB blood to type O blood in order to maintain large quantities of universal blood products.

In an attempt to increase the supply of type O blood, methods have been developed for converting types A, B and AB blood to type O blood. For example, U.S. Pat. No. 4,609,627 entitled "Enzymatic Conversion of Certain Sub-Type A and AB Erythrocytes" ("the '627 Patent"), is directed to a process for converting $A_{int}$ and $A_2$ (including $A_2B$ erythrocytes) to erythrocytes of the H antigen type, as well as to compositions of type B erythrocytes which lack A antigens, which compositions, prior to treatment, contained both A and B antigens on the surface of said erythrocytes. The process for converting $A_{int}$ and $A_2$ erythrocytes to erythrocytes of the H antigen type, which is described in the '627 Patent, includes the steps of equilibrating AB erythrocytes, contacting the equilibrated erythrocytes with α-N-acetylgalactosaminidase enzyme for a period sufficient to convert the A antigen to the H antigen, removing the enzyme from the erythrocytes and reequilibrating the erythrocytes.

The '627 Patent also discloses a method for purifying the α-N-acetylgalactosaminidase enzyme utilized in the conversion process. The disclosed purification procedure is extremely complicated and time-consuming and requires, in addition to several other steps, the extraction with acetone or the freeze drying of trimmed chicken livers in order to dehydrate the chicken livers. The procedure also requires the use of (1) a linear gradient to elute a protein fraction containing α-N-acetylgalactosaminidase, (2) two anion exchange columns, and (3) a BioGel P-150 column.

Further problems with the enzyme purification procedure described in the '627 Patent are that the procedure does not lend itself to large scale production. Hence, a need has arisen to develop a procedure for purifying enzymes which may then be capable of removing A antigens from the surface of cells in blood products which procedure is simple, efficient, lends itself to large scale use and produces an enzyme which is purer and has a higher specific activity.

In Levy et al., *Journal of Biological Chemistry*, Vol. 255, No. 24, dated Dec. 25, 1980, pages 11737–11742, isolation of α-N-acetylgalactosaminidase from *Clostridium perfringens* bacteria is described. However, the isolated bacterial α-N-acetylgalactosaminidase enzyme is not fully purified from contaminating sialidase, β-galactosidase, and β-N-acetylgalactosaminidase enzymes, making this preparation unsuitable for use in treating blood products for transfusion. Further, the bacterial enzyme described by Levy et al. achieved only a partial removal of A antigenicity, as evidenced by the fact that the cells treated with the bacterial enzyme agglutinated with human anti-A antiserum.

3

In "Glycosidases of Ehrlich Ascites Tumor Cells and Ascitic Fluid-Purification and Substrate Specificity of α-N-Acetylgalactosaminidase and α-Galactosidase: Comparison with Coffee Bean α-Galactosidase", by Yagi et al. in *Archives of Biochemistry and Biophysics*, Vol. 280, No. 1, dated July 1990, pages 61–67, the enzymes α-N-acetylgalactosaminidase and α-galactosidase were isolated from Ehrlich ascites tumor cells on ε-aminocaproylgalactosylamine-Sepharose. Again, the ascites α-N-acetylgalactosaminidase enzyme purified by Yagi et al. is not pure, as the enzyme shows more than one band on PAGE analysis. As stated on page 63 of the article, "neither the α-galactosidase nor the α-N-acetylgalactosaminidase [purified from Ehrlich ascite tumor cells] were homogeneous on polyacrylamide gel electrophoresis."

In addition, U.S. Pat. Nos. 4,427,777 and 4,330,619, as well as the article "Single-Unit Transfusions of RBC Enzymatically Converted from Group B to Group O to A and O Normal Volunteers", by Lenny et al. in Blood, Vol. 77, No. 6, Mar. 15, 1991, pages 1383–1388 are all directed to the purification and use of α-galactosidase enzyme for the removal of B antigens from erythrocytes. The paper entitled "Affinity Purification of α-galactosidase A from Human Spleen, Placenta and Plasma with Elimination of Pyrogen Contamination", by Bishop et al., in the *Journal of Biological Chemistry*, Vol. 286, No. 3, dated Feb. 10, 1981, pages 1307–1316 is directed to purification of α-galactosidase enzyme. However, to date, no method for purifying the enzyme α-N-acetylgalactosaminidase to homogeneity has been developed.

It is therefore an object of this invention to provide an improved method for purifying the enzyme α-N-acetylgalactosaminidase, which enzyme is capable of removing A antigens from the surface of cells in blood products.

It is another object of this invention to provide an improved method for purifying an enzyme capable of removing A antigens from the surface of cells in blood products, which method is simple and efficient, and can be used for large scale purification of said enzyme.

It is still another object of this invention to provide an enzyme capable of removing A antigens from the surface of cells in blood products wherein said enzyme is pure and homogeneous on polyacrylamide gel electrophoresis.

It is a further object of this invention to provide an enzyme capable of removing A antigens from the surface of cells in blood products, wherein said enzyme has a higher specific activity than enzymes previously purified.

The above brief description, as well as further objects and features of the present invention, will be more fully understood by reference to the following detailed description of the presently preferred, albeit illustrative, embodiments of the present invention.

SUMMARY OF THE INVENTION

This invention is directed to a method for purifying the enzyme α-N-acetylgalactosaminidase from avian liver, such enzyme being capable of removing A antigens from the surface of cells in blood products while allowing the structure and function of the cells to remain intact. The method of purifying the enzyme comprises homogenizing fresh or frozen-thawed avian livers with a buffer at a pH of 3.0–4.0, centrifuging, decanting the supernatant, slowly adding ammonium sulfate to a saturation of 30%, removing contaminating proteins in the resulting precipitate using filtration or centrifugation, adding ammonium sulfate to 50–70% saturation, pelleting the precipitate, dissolving it in buffer at a pH of 4.5–5.5, dialyzing against the same buffer and loading the dissolved precipitate onto a cation exchange column or resin. Examples of suitable cation exchange columns or resins include carboxymethyl (CM) cellulose, CM 52, CM agarose, CM sepharose and sulfophosphorous (SP) sephadex. Next, the cation exchange column or resin is washed, the enzyme-containing fraction eluted with a buffer at pH 4.5–5.5, and the eluted fraction is concentrated and dialyzed against a buffer at pH 4.5–5.5, and then applied to a column containing the affinity resin ε-aminocaproylgalactosylamine agarose. The resin is then washed in buffer, and the enzyme-containing fraction is eluted with N-acetylgalactosamine in buffer at a pH of 4.5–5.5, concentrated and subjected to molecular exclusion chromatography or gel filtration using a resin or filter with a molecular weight cutoff of at least approximately 100,000 daltons. This method of purification is simple and time efficient, and lends itself to large scale purification of α-N-acetylgalactosaminidase.

This invention is also directed to the enzyme purified by the method. The purified α-N-acetylgalactosaminidase enzyme is purified at least 2,300 fold and appears as a single homogenous band on SDS polyacrylamide gel electrophoresis, has a specific activity of 55–60 units/mg protein at pH 3.6 at 37° C, and displays intrinsic α-galactosidase activity (5–7%) of the α-N-acetylgalactosaminidase activity on a substrate unit/mg basis at pH 6.0 at 37° C.

DETAILED DESCRIPTION OF THE INVENTION

This invention is directed to the purification of an enzyme capable of removing A antigens from the surface of cells in blood products. The method of enzyme purification of this invention is simplified, time efficient and lends itself to large scale production. This invention is also directed to the a-N-acetylgalactosaminidase enzyme purified by the method of this invention. The enzyme is purified 2,300 fold, and exhibits a specific activity of 55–60 units/mg protein at pH 3.6 at 37° C. The isoelectric point of the enzyme purified by the method of this invention, as determined by chromatofocusing, is between 7.7 and 7.9. The purified enzyme, which is a glycoprotein, displays a single, homogenous band on SDS polyacrylamide gel electrophoresis. The purified enzyme displays intrinsic a-galactosidase activity (5–7% of the a-N-actelygalactosaminidase activity on a substrate unit/mg basis, assayed at pH 6.0 at 37° C). In addition, no detectable a-fucosidase, β-galactosidase, β-N-acetylglucosaminidase, neuraminidase or protease activity is found in said purified enzyme. Further, the a-N- acetylgalactosaminidase enzyme purified by the method of this invention is recyclable.

The method of purification comprises homogenizing fresh or frozen-thawed avian livers with a buffer at a pH of 3.0–4.0 (such as acetate, citrate or phosphate-citrate), centrifuging, decanting the supernatant, slowly adding ammonium sulfate to a saturation of 30%, removing contaminating proteins in the resulting precipitate using filtration or centrifugation, adding ammonium sulfate to 50–70% saturation, pelleting the precipitate, dissolving the precipitate in buffer at a pH of 4.5–5.5 (such as acetate, phosphate, phosphate-citrate, citrate or Tris-HCl), dialyzing against the same buffer and loading the solubilized precipitate onto a cation exchanger column or resin. Examples of cation exchangers are carboxymethyl (CM) cellulose, CM Sephadex, CM Sepharose and Sulfophosphorous (SP) Sephadex. Next, the cation exchanger column or resin is washed with buffer at a pH of 4.5–5.5, the enzyme-containing fraction eluted with a buffer at pH 4.5–5.5 (elution is accomplished by increasing the salt concentration of the buffer) and the eluted fraction is concentrated and dialyzed against a buffer at pH 4.5–5.5, and then applied to a column containing the affinity resin ε-aminocaproylgalactosylamine agarose. The affinity resin is when washed, and the enzyme eluted with N-acetylgalactosamine in buffer at a pH range of 4.5–5.5. The eluted enzyme is then concentrated and equilibrated in an isotonic buffer at a pH suitable for treatment of cells in blood products and subjected to gel filtration or molecular exclusion chromatography with a cutoff of at least approximately 100,000 molecular weight. Examples of resins suitable for this step include Sephadex G-100, Sepharose, Agarose, Sephacryl and Biogel.

EXAMPLE

Two hundred pounds of fresh or frozen-thawed chicken livers were trimmed of extraneous fat and then homogenized in a blender for 1–2 minutes with cold 0.1M citrate buffer pH 3.3 at a ratio of 1.8 liter buffer per 5 pounds liver. Any buffer with good buffering capacity in the pH range of 3.0–4.0 may be used instead of citrate buffer. In addition, the buffer to liver ratio can be in the range of 1.5–2.5 liters buffer per 5 pounds liver. The homogenate was then centrifuged, and the supernatant was decanted. Solid ammonium sulfate was slowly added ( so as not to cause denaturation) to a saturation of 30%. The resulting precipitate of contaminating proteins was centrifuged and ammonium sulfate was again added to a final concentration of 60% saturation. The precipitate was pelleted by centrifugation and dissolved in 0.01M sodium acetate pH 5.0. Any buffer with good buffering capacity in the range of 4.5–5.5 may be used. Appropriate salt concentration is in the range of 0.010 to 0.025M.

Next, the precipitate was dialyzed against the same buffer and loaded onto CM 52 cation exchanger resin in a 10×30 cm column. Following washing of the resin with 0.05M sodium acetate pH 5.0 ( again, any buffer at a higher salt concentration than the loading buffer with good buffering capacity in the pH range of 4.5–5.5 will do) the enzyme was eluted with 0.25M sodium acetate pH 5.0 (4.5–5.5). The eluted fraction was then concentrated and dialyzed against 50 mM sodium citrate pH 4.5 and applied to a column (3×20 cm) containing the affinity resin ε-aminocaproylgalactosylamine agarose. After washing with 0.25M NaCl in pH 4.5 buffer (the buffer may range from 4.0–5.5), elution of the precipitate was accomplished with 50 mM N-acetylgalactosamine in pH 4.5 buffer. At least 50 mM N-acetylgalactosamine should be used, with a pH range of 4.5–5.5. This fraction was then concentrated and equilibrated in phosphate buffered saline (PBS) at pH 6.0 (150 mM sodium chloride, 150 mM sodium phosphate) and subjected to gel filtration on Sephadex G 100 (Pharmacia).

RESULTS

As shown in Table I below, the main pool of the emerging α-N-acetylgalactosaminidase shows a 2300 fold total purification. The specific activity is 55–60 units/mg protein at pH 3.6 and 37° C. The isoelectric point of the enzyme, as determined by chromatofocusing, was between 7.7 and 7.9. The purified enzyme displayed intrinsic α-galactosidase activity (5–7% of the α-N-acetylgalactosaminidase activity on a substrate unit/mg basis, assayed at pH 6.0 and 37° C). There was no detectable α- fucosidase, β-galactosidase, β-N-acetylglucosaminidase, neuraminidase or protease activity. The purified enzyme displayed a single, homogeneous band on SDS acrylamide gel electrophoresis.

TABLE I

Purification of α-N-Acetylgalactosaminidase

Starting material = 200 lbs chicken liver

|  | Total Units | Spec. Activity | Total Recovery | Step Yield | Total Purification |
|---|---|---|---|---|---|
| Crude Homogenate | 50,000 | U/mg Protein 0.02 | 100% |  | 1 |
| 30–60% (NH$_4$)$_2$SO4 ppt | 36,000 | 0.10 | 72% | 72% | 5 |
| CM 52 | 32,500 | 0.5 | 65% | 90% | 25 |
| Affinity | 26,000 | 35 | 52% | 80% | 1750 |
| *Seph G100 | 18,000 | 55–60 | 36% | 75% | 2300 |

*This step yields a side fraction containing 5000 units of the enzyme which can be reapplied to the next G100 column.
1 Unit of enzyme liberates 1 micromole α-N-acetylgalactosamine per min at 37° C. and pH 3.6.

The α-N-acetylgalactosaminidase enzyme purified by the method of this invention was used to treat blood type A red blood cells. The reactivity of α-N-acetylgalactosaminidase-treated type A red blood cells with human polyclonal anti-A serum was then determined. The results are shown in Table II below. A decrease in reactivity with polyclonal anti-A antibody reflects removal of the type $A_1$ and type $A_2$ antigens from the surface of the red blood cells by the α-N-acetylgalactosaminidase enzyme purified by the method of this invention.

TABLE II

|  | Polyclonal anti-A titer | |
|---|---|---|
|  | Type $A_1$ | Type $A_2$ |
| Untreated cells | 512/1024 | 512 |
| Treated cells | 8/16 | non reactive |

The method of this invention used to purify α-N-acetylgalactosaminidase from avian liver is simple and time efficient. In addition, as can be seen in Table I, the enzyme purified by said method is highly purified (2,300 fold purification) and has a high specific activity (55–60 units/mg protein). Said purified enzyme may be used to remove A antigens from the surface of cells in blood products. Methods for converting types A and AB blood products to type O blood products using a purified enzyme capable of removing A antigens from the surface of erythrocytes can be found in U.S. Pat. No. 4,609,627 issued Sep. 2, 1986 to Goldstein, entitled "Enzymatic Conversion of Certain Sub-Type A and AB Erythrocytes", which is incorporated herein by reference.

Although the invention herein has been described with reference to particular embodiments, it is to be understood that these embodiments are merely illustrative of the various aspects of the invention. Thus, it is to be understood that numerous modifications may be made in the illustrative embodiments and other arrangements may be devised without departing from the spirit and scope of the invention.

We claim:

1. A method for purifying α-N-acetylgalactosaminidase enzyme from avian liver consisting essentially of the steps of:

(a) homogenizing fresh or frozen-thawed avian liver in a buffer having a pH of about 3.0–4.0 and comprising acetate, citrate, phosphate or phosphate-citrate, centrifuging said homogenate to obtain a supernatant, and decanting the supernatant;

(b) adding ammonium sulfate to the decanted supernatant to a saturation of about 30% to form a first precipitate containing contaminating proteins, removing the first precipitate, adding ammonium sulfate to the supernatant to a saturation of about 50–70% to obtain a second precipitate comprising the enzyme, and recovering the second precipitate;

(c) dissolving the second precipitate in a buffer having a pH of about 4.5–5.5 and comprising acetate, phosphate, phosphate-citrate, citrate or Tris-HCl, and dialyzing against the same buffer;

(d) applying the dialyzed precipitate to a cation exchange column;

(e) washing the cation exchange column with a buffer having a pH of about 4.5–5.5 and comprising acetate, phosphate, phosphate-citrate, citrate or Tris-HCl at a concentration of about 0.05M, eluting the enzyme-containing fraction with a buffer having a pH of about 4.5–5.5 and comprising acetate, phosphate, phosphate-citrate, citrate or Tris-HCl at a concentration of about 0.25M, and concentrating and dialyzing the eluted enzyme-containing fraction;

(f) applying the dialyzed enzyme-containing fraction to a column containing an ε-aminocaproylgalactosylamine agarose affinity resin;

(g) washing the affinity resin with a buffer having a pH of about 4.0–5.5 and a salt concentration of about 0.25M, eluting the enzyme with a buffer having a pH of about 4.5–5.5 and comprising at least 50 mM N-acetylgalactosamine, and concentrating and equilibrating the eluted enzyme; and (h) subjecting the concentrated, eluted enzyme to gel filtration or molecular exclusion chromatography with a resin having a molecular weight cutoff of approximately 100,000 daltons, and recovering the enzyme subjected thereto.

2. The method of claim 1, wherein the avian liver is selected from the group consisting of chicken, turkey, and pigeon liver.

3. The method of claim 1, wherein the buffer in step (a) comprises sodium citrate.

4. The method of claim 3, wherein the concentration of the sodium citrate is about 0.1M.

5. The method of claim 4, wherein the pH of the buffer is about 3.3.

6. The method of claim 1, wherein the buffer in step (c) comprises sodium acetate.

7. The method of claim 6, wherein the concentration of sodium acetate is about 0.01M.

8. The method of claim 7, wherein the pH of the buffer is about 5.0.

9. The method of claim 1, wherein the cation exchange column in step (d) is carboxymethyl (CM) cellulose, CM agarose, CM Sephadex, CM Sepharose, or Sulfophosphorous (SP) Sephadex.

10. The method of claim 9, wherein the cation exchange column is CM52.

11. The method of claim 1, wherein the washing buffer in step (e) comprises sodium acetate.

12. The method of claim 11, wherein the buffer has a pH of about 5.0.

13. The method of claim 1, wherein the eluting buffer in step (e) comprises sodium acetate.

14. The method of claim 13, wherein the buffer has a pH of about 5.0.

15. The method of claim 1, wherein eluted enzyme-containing fraction is concentrated and dialyzed in step (e) against a buffer having a pH of about 4.5–5.5 and comprising acetate, phosphate, phosphate-citrate, citrate or Tris-HCl.

16. The method of claim 15, wherein the buffer comprises sodium citrate.

17. The method of claim 16, wherein the sodium citrate has a concentration of about 50 mM.

18. The method of claim 17, wherein the buffer has a pH of about 4.5.

19. The method of claim 1, wherein the washing buffer in step (g) comprises NaCl.

20. The method of claim 19, wherein the buffer has a pH of about 4.5.

21. The method of claim 1, wherein the N-acetylgalactosamine in step (g) has a concentration of 50 mM.

22. The method of claim 21, wherein the eluting buffer has a pH of about 4.5.

23. The method of claim 1, wherein the eluted enzyme is concentrated and equilibrated in step (g) with phosphate buffered saline (PBS) at a pH of about 6.0.

24. The method of claim 1, wherein the resin in step (h) is Sephadex G-100, Sepharose, agarose, Sephacryl, or Biogel.

25. The method of claim 24, wherein the resin is Sephadex G-100.

* * * * *